US011999931B2

(12) United States Patent
Jonas et al.

(10) Patent No.: US 11,999,931 B2
(45) Date of Patent: Jun. 4, 2024

(54) HIGH-THROUGHPUT SYSTEM AND METHOD FOR THE TEMPORARY PERMEABILIZATION OF CELLS

(71) Applicants: THE REGENTS OF THE UNIVERSITY OF CALIFORNIA, Oakland, CA (US); PRESIDENT AND FELLOWS OF HARVARD COLLEGE, Cambridge, MA (US); THE BRIGHAM AND WOMEN'S HOSPITAL, INC., Boston, MA (US)

(72) Inventors: Steven J. Jonas, Hawthorne, CA (US); Paul S. Weiss, Los Angeles, CA (US); Xu Hou, Fujian (CN); Joanna Aizenberg, Boston, MA (US); Alireza Khademhosseini, Cambridge, MA (US)

(73) Assignees: THE REGENTS OF THE UNIVERSITY OF CALIFORNIA, Oakland, CA (US); PRESIDENT AND FELLOWS OF HARVARD COLLEGE, Cambridge, MA (US); THE BRIGHAM AND WOMEN'S HOSPITAL, INC., Boston, MA (US)

( * ) Notice: Subject to any disclaimer, the term of this patent is extended or adjusted under 35 U.S.C. 154(b) by 1252 days.

(21) Appl. No.: 16/324,535

(22) PCT Filed: Aug. 19, 2017

(86) PCT No.: PCT/US2017/047692
§ 371 (c)(1),
(2) Date: Feb. 8, 2019

(87) PCT Pub. No.: WO2018/039084
PCT Pub. Date: Mar. 1, 2018

(65) Prior Publication Data
US 2019/0177677 A1 Jun. 13, 2019

Related U.S. Application Data

(60) Provisional application No. 62/377,572, filed on Aug. 20, 2016.

(51) Int. Cl.
C12M 1/00 (2006.01)
C12M 1/42 (2006.01)
(Continued)

(52) U.S. Cl.
CPC ............ *C12M 23/16* (2013.01); *C12M 23/20* (2013.01); *C12M 23/58* (2013.01); *C12M 29/00* (2013.01);
(Continued)

(58) Field of Classification Search
None
See application file for complete search history.

(56) References Cited

U.S. PATENT DOCUMENTS 9,121,307 B2    9/2015   Aizenberg et al.
9,353,646 B2    5/2016   Aizenberg et al.
(Continued)

FOREIGN PATENT DOCUMENTS

WO    WO 2013/059343 A1    4/2013
WO    WO 2014/145528 A1    9/2014
(Continued)

OTHER PUBLICATIONS

Hosono, et al. "Superhydrophobic Perpendicular Nanopin Film by the Bottom-Up Process" Journal of the American Chemical Society 2005 127 (39), 13458-13459 DOI: 10.1021/ja053745j (Year: 2005).*
(Continued)

*Primary Examiner* — Holly Kipouros
*Assistant Examiner* — Nathan G Esperon
(74) *Attorney, Agent, or Firm* — VISTA IP LAW GROUP LLP

(57) ABSTRACT

A microfluidic device for processing cells for the intracellular delivery of molecules or other cargo includes a plural-
(Continued)

ity of microchannels disposed in a substrate or chip and fluidically coupled to an inlet configured to receive a solution containing the cells and the molecules or other cargo to be delivered intracellularly to the cells. Each of the plurality of microchannels has one or more constriction regions therein, wherein the constriction regions comprise an omniphobic, superhydrophilic, or superhydrophobic surface. In some embodiments, multiple microfluidic devices operating in parallel are used to process large numbers of cells. The device and method has particularly applicability to delivering gene-editing molecules intracellularly to cells.

10 Claims, 4 Drawing Sheets

(51) Int. Cl.
*C12M 3/06* (2006.01)
*C12N 15/90* (2006.01)

(52) U.S. Cl.
CPC ........... *C12M 35/04* (2013.01); *C12N 15/907* (2013.01); *C12N 2310/20* (2017.05)

(56) References Cited

U.S. PATENT DOCUMENTS

| | | | |
|---|---|---|---|
| 2005/0036918 A1* | 2/2005 | Lange | B01L 3/5027 422/400 |
| 2007/0037172 A1 | 2/2007 | Chiu et al. | |
| 2010/0116343 A1* | 5/2010 | Weibel | F16K 99/0001 137/329 |
| 2011/0104730 A1* | 5/2011 | Larsen | C12M 21/06 435/243 |
| 2011/0250692 A1 | 10/2011 | Yamanaka et al. | |
| 2012/0181346 A1* | 7/2012 | Greer | C03C 17/006 264/293 |
| 2013/0171628 A1 | 7/2013 | Di Carlo et al. | |
| 2013/0309679 A1 | 11/2013 | Ismagilov et al. | |
| 2014/0147627 A1* | 5/2014 | Aizenberg | F15D 1/02 428/141 |
| 2014/0287509 A1* | 9/2014 | Sharei | C12N 5/0602 435/375 |
| 2015/0004692 A1 | 1/2015 | Le Berre et al. | |
| 2015/0152270 A1 | 6/2015 | Aizenberg et al. | |
| 2016/0047735 A1* | 2/2016 | Grisham | G01N 15/1484 435/7.1 |
| 2018/0003696 A1 | 1/2018 | Sharei et al. | |
| 2018/0245089 A1 | 8/2018 | Sharei et al. | |

FOREIGN PATENT DOCUMENTS

| | | | | |
|---|---|---|---|---|
| WO | WO 2015/023982 A1 | 2/2015 | | |
| WO | WO 2015/054652 A2 | 4/2015 | | |
| WO | WO 2015/054652 A3 | 4/2015 | | |
| WO | WO-2015054652 A2 * | 4/2015 | ............... | C09D 5/00 |
| WO | WO 2016/115179 A1 | 7/2016 | | |
| WO | WO 2017/008063 A1 | 1/2017 | | |
| WO | WO 2017/123663 A1 | 7/2017 | | |

OTHER PUBLICATIONS

PCT International Search Report for PCT/US2017/047692, Applicant: The Regents of the University of California, Form PCT/ISA/210 and 220, dated Oct. 27, 2019 (3pages).
PCT Written Opinion of the International Search Authority for PCT/US2017/047692, Applicant: The Regents of the University of California, Form PCT/ISA/237, dated Oct. 27, 2017 (7pages).
Alison, Grinthal et al., Mobile Interfaces: Liquids as a Perfect Structural Material for Multifunctional, Antifouling Surfaces, Chem. Mater. 26, No. 1: 698-708. DOI: 10.1021/cm402364d (2013).
Epstein, Alexander K. et al., Liquid-infused structured surfaces with exceptional anti-biofouling performance, www.pnas.org/cgi/doi/10.1073/pnas.1201973109, PNAS Early Edition (2012) (6pages).
Hallow, Daniel M. et al., Shear-induced intracellular loading of cells with molecules by controlled microfluidics, Biotechnol Bioeng. Mar. 1, 2008; 99(4): 846-854, doi:10.1002/bit.21651.
Han, Xin et al., CRISPR-Cas9 delivery to hard-to-transfect cells via membrane deformation, Sci. Adv. 2015; 1: e1500454, Aug. 14, 2015 (8pages).
Sharei, Armon et al., A vector-free microfluidic platform for intracellular delivery, 2082-2087, PNAS, Feb. 5, 2013, vol. 110, No. 6, www.pnas.org/cgi/doi/10.1073/pnas.1218705110.
Tesler, Alexander B. et al., Extremely durable biofouling-resistant metallic surfaces based on electrodeposited nanoporous tungstite films on steel, Nature Communications, 6:8649, DOI: 10.1038/ncomms9649/www.nature.com/naturecommunications (2015).
Wong, Tak-Sing et al., Bioinspired self-repairing slippery surfaces with pressure-stable omniphobicity, Sep. 22, 2011, vol. 477, Nature, 443-447.
Hou, Xu et al., Fluid-Based Gating Mechanism with Tunable Multiphase Selectively and Antifouling Behavior, Nature 519, No. 7541:70-73, doi:10.1038/nature14253 (2015).
Communication pursuant to Article 94(3) EPC dated Apr. 14, 2021 for European Patent Application No. 17844190.3-1118, (5 pages).
Reply to communication pursuant to Article 94(3) EPC dated May 11. 2021 for European Patent Application No. 17844190.3-1118, (29 pages).
Communication Communication under Rule 71(3) dated Mar. 4, 2022 for European Patent Application No. 17844190.3-1118, (7 pages).
PCT International Preliminary Report on Patentability (Chapter I of the Patent Cooperation Treaty) for PCT/US2017/047692, Applicant: The Regents of the University of California et al., Form PCT/IB/326 and 373, dated Mar. 7, 2019 (9pages).
Supplementary Search Report dated Jul. 24, 2019 in European Patent Application No. 17844190.3 (8pages).
Gogolides, Evangelos et al., Hierarchical micro and nano structured, hydrophilic, superhydrophobic and superoleophobic surfaces incorporated in microfluidics, microarrays and lab on chip microsystems, Microelectronic Engineering 132 (2015) 135-155.
Sharei, Armon et al., A vector-free microfluidic platform for intracellar delivery, 2082-2087, PNAS, Feb. 5, 2013, vol. 110, No. 6.
Communication pursuant to Rules 70(2) and 70a(2) EPC dated Aug. 9, 2019 European Patent Application No. 17844190.3 (1page).
Response to extended European search report dated Feb. 17, 2020 in European Patent Application No. 17844190.3 (10pages).
Reply to Communication Communication under Rule 71(3) dated Jul. 14, 2022 for European Patent Application No. 17844190.3-1118, (8 pages).

* cited by examiner

HIGH-THROUGHPUT SYSTEM AND METHOD FOR THE TEMPORARY PERMEABILIZATION OF CELLS

RELATED APPLICATION

This Application is a U.S. National Stage filing under 35 U.S.C. § 371 of International Application No. PCT/US2017/047692, filed Aug. 19, 2017, which claims priority to U.S. Provisional Patent Application No. 62/377,572 filed on Aug. 20, 2016, which are hereby incorporated by reference. Priority is claimed pursuant to 35 U.S.C. §§ 119, 371 and any other applicable statute.

TECHNICAL FIELD

The technical field generally relates to devices and methods that are used to deliver molecules or other cargo into cells at clinically relevant scales. The technical field has particular suitability for the delivery of gene-editing constructs or biomolecules into large numbers of cells. In particular, the invention relates to microfluidic devices that use omniphobic and/or fouling-resistant microchannels that have constrictions therein to temporarily permeabilize cells that aid in the introduction and transfer of molecules or other cargo from the surrounding fluid into the cells.

BACKGROUND

Gene therapy and gene modification technologies are increasingly being studied, investigated, and used for clinical applications. In order to modify or alter genes, the gene-editing biomolecules or other constructs need to be delivered into cells. Currently, a standard technique for gene modification uses virus-based delivery systems that utilize, for example, lentiviruses, adenoviruses, adeno-associated viruses, or herpes virus. Lentiviruses, for instance, can deliver a significant amount of genetic information into DNA of the host cell so they are one of the most effective and commonly used methods of a gene delivery vector. The use of viral transfection, while effective as a vector system, is expensive and has potential serious adverse side effects. Principal among the possible dangers with virus-based delivery systems is the fact that integration of genetic modifications occurs semi-randomly, leading to concern for potential genotoxicity and carcinogenesis through off-target effects.

Electroporation, in which an electrical field is applied to cells in order to increase the permeability of the cell membrane, is another technique that has been used to transfect cells for gene therapy based on targeted endonucleases. Conventional electroporation, however, suffers from toxicity problems as well as technical limitations in using this method in scaled-up clinical applications. Chemical transfection methods may also be used for gene-editing applications based on targeted endonucleases.

Still other approaches for the intracellular delivery of biomolecules involving nanoparticles or nanostructures (e.g., nanostraws, carbon nanotubes, or needles) have been demonstrated but have not been commercialized or scaled up for clinical use. Intracellular delivery of biomolecules by cell membrane deformation within microfluidic channels has been demonstrated. For example, U.S. Patent Application Publication No. 2014/0287509 discloses a microfluidic system for causing temporary pertubations in the cell membrane using a cell-deforming constriction in the microfluidic channel. In another approach, a series of microconstrictions are generated by a pattern of protuberances that extend from a polydimethylsiloxane (PDMS) to apply shear and compressive forces on cells passing therethrough. See Han et al., CRISPR-Cas9 delivery to hard-to-transfect cells via membrane deformation., Sci. Adv., pp. 1-8 (2015).

While the intracellular delivery through cell membrane deformation is beginning to emerge, current embodiments of this technology suffer from issues with fouling or clogging, which affects the long-term reliability of the device and efforts for translation towards clinicaly relevant applications. For example, in clinical gene therapy, large numbers of cells need to be transfected (e.g., billions of cells) rapidly. Current technologies are not adapted for such large scale processing because they tend to become quickly fouled or clogged. For example, it is not uncommon for a microfluidic device to become clogged with cells after just seconds or minutes of operation.

SUMMARY

In one embodiment, a microfluidic-based system for the intracellular transport of molecules or other cargo is disclosed. The system includes a microfluidic substrate or chip that includes therein a plurality of microchannels that contain one or more constrictions that are dimensioned to induce a transient increase in the permeability of cells that pass through the constrictions. The microchannels may be arranged in parallel in the substrate or chip (or multiple substrates or chips) (e.g., an array) so that cells may be processed in parallel fashion in a plurality of microchannels. In this regard, large numbers of cells may be processed so that useful quantities of transfected cells may be used for clinical applications.

The dimensions of the constrictions may vary but is typically between around 30% to around 90% smaller than the diameter or largest dimension of the cell of interest that is flowed through the microchannel. In one particular embodiment of the invention, the constriction has a width within the range between about 4 µm to 10 µm. In order to prevent fouling and/or clogging of the microchannels at the constriction, the constriction contains a surface with omniphobic, superhydrophilic, superhydrophobic, or anti-fouling characteristics or properties. For example, one particular embodiment may utilize microchannels having slippery liquid-infused porous surfaces (SLIPS). In SLIPS, a porous or textured solid contains an immobilized lubricant film that exhibits omniphobic properties. For example, a porous substrate formed from a polymeric or elastomeric material may be infused or loaded with a chemically-matched fluid such as an oil to create a SLIPS interface. An aqueous-based fluid that contains the cells is then run through the microchannels. The aqueous fluid that carriers the cells may contain the molecules or other cargo that is to be intracellularly delivered to the cells during the transitory state in which the cell membrane becomes permeable. As one particular example, biomolecules or gene-editing cargo materials are delivered into the permeable cells from the surrounding solution, which may be mixed with the cells or delivered separately.

In another embodiment, the constriction regions in the microfluidic device may contain on their inner or contact surfaces a plurality of nanofeatures that are sculpted or otherwise formed within the microchannels. The nanofeatures, which in some embodiments, may include sharp nanometer-sized structures, can be used in conjunction with a SLIPS layer to impart better anti-fouling properties. In particular, in some embodiments, the thickness of this lubricant layer can be adjusted to selectively expose or mask entirely the nanofeatures disposed on the surface to alter the surface characteristics of the microchannel.

In another embodiment, a microfluidic device for processing cells includes a substrate or chip having a plurality of microchannels disposed therein, the microchannels being fluidically coupled to an inlet configured to receive a solution containing the cells as well as molecules or other cargo to be delivered intracellularly to the cells, each of the plurality of microchannels containing a constriction region therein, wherein the microchannels including the constriction region comprise an omniphobic, superhydrophilic, or superhydrophobic surface. In some embodiments, the omniphobicity, hydrophilicity, or hydrophobicity may be created by a film or layer of lubricant that is disposed on the inner surface of the microchannel forming the constriction region. In some embodiments, the constriction may also include a plurality of nanofeatures that extend or project into the flow path created in the constriction region. The nanofeatures may, in some embodiments, comprise sharpened or pointed tips to aid in permeabilizing the cells.

In another embodiment, a method of delivering gene-editing molecules to cells includes flowing a solution containing the cells and the gene-editing molecules or other cargo through a plurality of microchannels formed in a microfluidic device or chip, wherein each of the microchannels comprises one or more constriction regions, wherein the one or more constriction regions comprise a surface rendered superhydrophobic, superhydrophilic, or omniphobic. The surface may be rendered resistant to fouling. This may be accomplished by rendering the surface superhydrophobic, superhydrophilic, or omniphobic using any of the methods or techniques described herein. Further, in some embodiments, cells and gene-editing molecules or other cargo are flowed through a plurality of microfluidic devices or chips to increase the number of cells that can be processed.

BRIEF DESCRIPTION OF THE DRAWINGS

FIG. 2 illustrates a two-layer device although it should be appreciated that additional layers may be employed in other embodiments.

DETAILED DESCRIPTION OF THE ILLUSTRATED EMBODIMENTS

Figure 1:
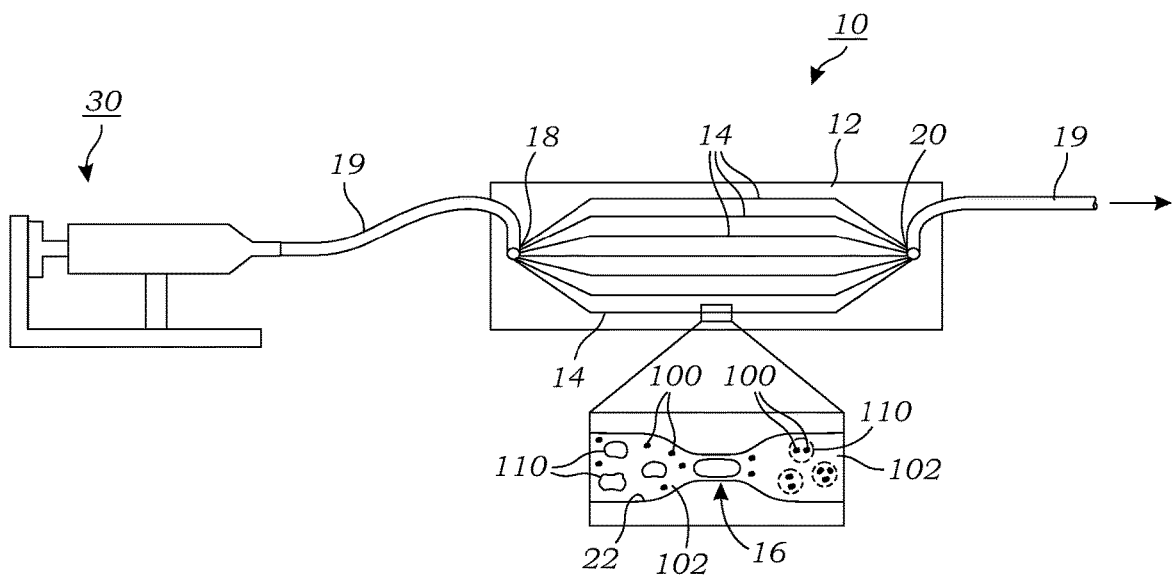
FIG. 1 schematically illustrates a microfluidic-based system for the intracellular transport of molecules or other cargo into cells. Also illustrated is a constriction or constriction region that is located in one of the microchannels.

FIG. 1 illustrates a microfluidic-based system 10 for the intracellular transport of molecules or other cargo 100 into cells 110. The system 10 includes a microfluidic substrate or chip 12 that includes therein a plurality of microchannels 14 that contain one or more constrictions 16 or (constriction regions) that are dimensioned to induce a transient increase in the permeability of cells 110 that pass through the constrictions 16. The microfluidic substrate or chip 12 includes at least one inlet 18 and at least one outlet 20 that are fluidically coupled to a plurality of microchannels 14 that are formed within the microfluidic substrate or chip 12. Tubing 19 may be connected to the at least one inlet 18 and the at least one outlet 20 as illustrated. The microchannels 14 form a fluidic path through the microfluidic substrate or chip 12. Generally, the microchannels 14 are rectangular or square in cross-sectional shape and have cross-sectional dimensions that are less than about 1 mm, although it should be understood that other geometric shapes may be used in the microfluidic system 10 described herein. Typically, the cross-sectional dimension of the microchannels 14 at their largest dimension is less than about 250 µm. More typically, the microchannels 14 have a diameter or width that is less than about 50 µm in some embodiments (e.g., around 25 µm×25 µm). The microchannels 14 are dimensioned so as to accommodate the passage of cells 110 contained within a carrying fluid 102. The cells 110 are typically eukaryotic cells and more specifically eukaryotic cells obtained from a mammal. Cells 110 may have a range of sizes but typically have a diameter or largest dimension within the range of around 5 µm to around 20 µm. The length of the microchannels 14 may also vary. The length of the microchannels 14 may be tens or hundreds of microns in length or up to several or tens of centimeters in length.

The microchannels 14 may be linear in shape as illustrated in FIG. 1 or they have other configurations such as being curved, spiraled, serpentine, or the like. As seen in FIG. 1, a plurality of microchannels 14 are provided in a single microfluidic substrate or chip 12 to enable parallel processing of cells 110. As seen in FIG. 1, each microchannel 14 contains one or more constrictions 16 located along a length of the microchannel 14. The width (W) of the constriction 16 (FIG. 4) is formed so as to subject the cells 110 to a transient compression or stretching of the cell 110 that temporarily increases the permeability of the cellular membrane of the cells 110 such that the cells 110 uptake the extracellular molecules or cargo 100 that are contained in the surrounding fluid 102. The uptake of the extracellular molecules or cargo 100 is vector-free and is diffusion based. The width (W) of the constriction 16 may vary but is generally less than about 10 µm. For example, the width of the constriction 16 may include 4 µm, 5 µm, 6 µm, 7 µm, or 9

μm. Of course, for larger cells 110, the width (W) of the constriction 16 may be larger and above 10 μm. The key aspect is that the constriction impart upon the passing cells 110 a rapid and temporary stretching or compression that increases the permeability of the cellular membrane. Typically, the constriction 16 may have a width (W) that is about 30% to about 90% smaller than the diameter of the cell 110 of interest. The length (L) (FIG. 4) of the constriction 16 may vary but is typically within the range of about 10 μm to about 100 μm.

Generally, the increased permeability of cellular membrane of the cell 110 lasts hundreds of seconds to several minutes (e.g., about 4-10 minutes is common). As the molecules or other cargo 100 travel with the cells 110 through the microchannels 14, they are incorporated intracellularly via diffusion across pores formed in the cell membrane established as the cells 110 pass through the constrictions 16.

Figure 3:
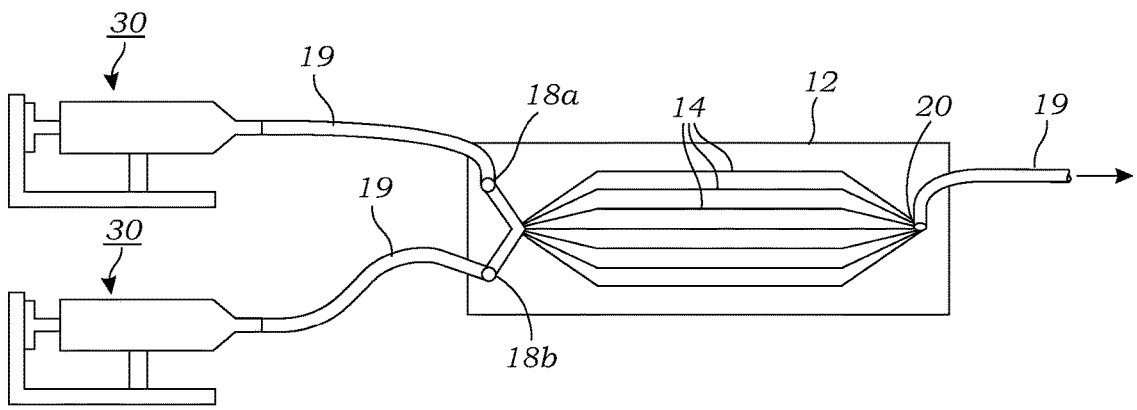
FIG. 3 schematically illustrates a microfluidic-based system for the intracellular transport of molecules or other cargo into cells. In this embodiment, separate pumps are used to pump the cells and the molecules or other cargo that is to be transported into the cells.

As seen in FIG. 1, the molecules or other cargo 100 are initially present within a carrier fluid 102 and are located outside or extracellular with respect to the cells 110. The molecules or other cargo 100 may be added to a culture medium or buffer solution that surrounds the cells 110 and this mixture may be delivered via a common inlet 18 such as that illustrated in FIG. 1. Alternatively, as seen in the embodiment of FIG. 3, the microfluidic substrate or chip 12 may have a first inlet 18a that is that is used to deliver cells 110 and a second inlet 18b that is used to deliver the molecules or other cargo 100. As seen in FIGS. 1 and 3, the microfluidic substrate or chip 12 is coupled to one or more pumps 30 that are used to pump the cells 110 and the molecules or other cargo 100 through the microchannels 14. Any number of types of pumps 30 known to those skilled in the art may be used including, for example, syringe pumps, peristaltic pumps, and the like. The pumps 30 may be controlled or adjustable to modify the flow rate of fluid through the microchannels 14. Generally, the flow rate of fluid 102 through the microchannels 14 is less than 1 mL/minute per microchannel 14. Higher flow rates will produce higher throughputs through the system 10. According to one preferred embodiment of the invention, flow rates that achieve cell processing rates between about 50 and about 100,000 cells/sec/microchannel are used.

The molecules or other cargo 100 may include any number of biomolecules. These include, by way of example, proteins, enzymes, nucleic acids (e.g., DNA, RNA), plasmids, and viruses. Molecules or other cargo 100 may also include one or more labels or dyes that may be used to target individual cell types or intracellular organelles or cell products. In one particular embodiment, the molecules or other cargo 100 include gene-editing molecules that alter the genetic makeup of the cells 110. One particular example of gene-editing molecules includes the CRISPR-Cas9 nuclease system that includes single-guide RNA (sgRNA) and the enzyme Cas9. The sgRNA directs the Cas9 nuclease to introduce sequence-specific targeted insertions, deletions, and genetic edits at specific genetic targets.

Figure 2:
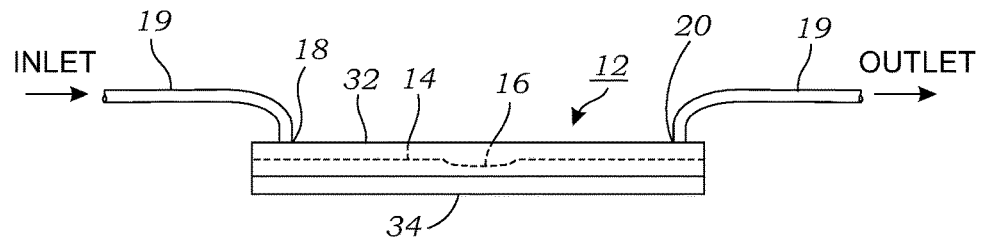
FIG. 2 is a side view of one illustrative construction of the microfluidic substrate or chip that is used as part of the microfluidic-based system.

FIG. 2 illustrates the construction of the microfluidic substrate or chip 12 according to one embodiment. In this embodiment, the microfluidic substrate or chip 12 is formed from a laminate structure having multiple layers that adhered or otherwise bonded to one another. As seen in FIG. 2, a first layer 32 of the device has the microchannels 14 with constrictions 16 formed therein that is bonded or adhered to a second layer 34 that serves as the bottom (or top) of the device. The at least one inlet 18 and at least one outlet 20 are also formed in the first layer 32. Tubing 19 may be connected to the inlet 18 and outlet 20 as illustrated. In one embodiment of the microfluidic substrate or chip 12, both the first layer 32 and the second layer 34 are formed from the same material. In another embodiment, the first layer 32 may be formed from a first material while the second layer 34 is formed from a second, different material.

In some embodiments of the microfluidic substrate or chip 12, one or more the surfaces 22 of the microchannel 14 that are exposed to the fluid 102 environment containing the cells 110 are characterized as superhydrophobic. Superhydrophobic is meant to indicate that the surface has a contact angle with water that is 150° or greater and exhibits low contact angle hysteresis. In some other embodiments, the microfluidic substrate or chip 12 includes one or more surfaces 22 of the microchannel 24 that are characterized as superhydrophilic. Superhydrophilic is meant to indicate that that the surface has a contact angle with water that is equal to about 5-10° or less. Superhydrophilic surfaces may be created by deposition, modification of surface chemistry, surface roughening or the like.

In another embodiment of the microfluidic substrate or chip 12, one or more surfaces 22 of the microchannels 14 that are exposed to the fluid 102 environment containing the cells 110 are rendered omniphobic. Omniphobic refers to a microchannel 14 surface that repels both aqueous and oil-based fluids. For example, an omniphobic surface may display contact angles of 150° and low contact angle hysteresis with both polar and non-polar liquids. In one embodiment, the first layer 32 and/or second layer 34 are formed from a porous or textured polymer or amorphous material that is capable of being infused or loaded with a lubricant 36 (seen in FIGS. 4, 6, and 7). The lubricant 36, in some embodiments, is immiscible with the carrier fluid 102. For example, the first layer 32 and/or the second layer 34 may be formed using polytetrafluoroethylene, polydimethylsiloxane (PDMS), copolymers of urea and PDMS (uPDMS), glass, silicon, polyester, carbon, polyethersulfone, polyvinylidenedifluoride (PVDF), aliphatic or semi-aromatic polyamides. In one particular embodiment, the lubricant 36 contained in the first layer 32 and/or the second layer 34 creates an omniphobic film or layer on the surface 22 of the constriction 16 (and also optionally in the microchannel 14) that reduces fouling and/or clogging of the constriction 16 and/or the microchannels 14. The surface 22 is thus rendered omniphobic and may exist on all exposed surfaces of the microchannel 14 and constriction 16 (e.g., all four sides) or one fewer than all sides (e.g., three sides, two sides, or one side). The omniphobic rendered surface 22 may be present only in the region of the constrictions 16 or, alternatively, the omniphobic rendered surface 22 may be located on substantially the entire length of the microchannels 14. In some embodiments, the porous or textured material used for the microfluidic substrate or chip 102 is functionalized with one or more chemical groups to improve the adherence or affinity to the lubricant 36 and aid in creating a stable, immobilized layer on the surface 22 as described herein.

The lubricant 36 that is infused or loaded in the first layer 32 and/or second layer 34 may include, in one embodiment, an oil-based material. These include by way of example, oils such as mineral oils, olive oil, canola oil, coconut oil, corn oil, rice-based oils, cottonseed oil, grape seed oil, hemp oil, mustard oil, palm oil, peanut oil, pumpkin seed oil, safflower oil, sesame oil, soybean oil, sunflower oil, tea seed oil, walnut oil, and mixtures of the same. Perfluorinated fluids may also be used as the lubricant. Examples include, tertiary perfluoroalkylamines such as perfluorotri-n-pentylamine, FC-70 Fluorinert™ by 3M, perfluorotri-n-butylamine FC-40

Fluorinert™, etc.), perfluoroalkylsulfides and perfluoroalkylsulfoxides, perfluoroalkylethers, perfluorocycloethers (like FC-77 Fluorinert™) and perfluoropolyethers (such as KRYTOX™ family of lubricants by DuPont; e.g., KRYTOX™ 103), perfluoroalkylphosphines and perfluoroalkylphosphine oxides as well as their mixtures. The lubricant 36 may also include ionic liquids, hydrocarbons, and silicone oil.

The lubricant 36 may be loaded into the first layer 32 and/or the second layer 34 using any number of methods. For example, the first layer 32 and/or the second layer 34 may be soaked or otherwise exposed to the lubricant 36 by submerging the same in a bath of lubricant 36. This can be done prior to assembly or post-assembly. In addition, the first layer 32 and/or second layer 34 may be infused with the lubricant 36 by flowing the lubricant 36 through the microchannels 14 by pumping or introducing the lubricant 36 through the microfluidic device 12 using the one or more inlets 18. For example, for a PDMS-based microfluidic device 12, silicone oil (10 cSt) may be pumped through the microchannel 14 at a flow rate of 0.0001-0.0005 mL/min for about 2-20 hours.

The microchannels 14 as well as the constriction 16 may be formed using any number of methods including three-dimensional printing, laser cutting, mechanical cutting, soft lithography, pipette pulling, or thermal molding. In one particular method of making the microchannels 14, a direct casting method is employed. In the direct casting method of fabrication, a two-part liquid curable solution in a 1:1 vol/vol ratio is mixed and poured over a photolithographically prepared master mold (e.g., silicon mold, glass capillaries) that contains relief structures that that form the microchannels 14 and constriction regions 16 in the first layer 32. As one illustrative example, the two-part mixture uses mixture SM47i-02 (Parts A and B) available from SLIPS Technologies, Cambridge, Mass. SM47i-02 Part A is a mixture that includes vinyl modified Q silica resin, vinyl terminated polydimethylsiloxane, trifluromethyl C1-4 alkyl dimethicone, platinum 1,3-diethenyl-1,1,3,3-tetramethyldisiloxane complexes, monovinyl terminated polydimethylsiloxane, and divinyltetramethyldisiloxane. Part B is a mixture that includes vinyl modified Q silica resin, vinyl terminated polydimethylsiloxane, methylhydrosiloxane—dimethylsiloxane copolymer, trimethylsiloxane terminated, trifluromethyl C1-4 alkyl dimethicone.

The two-part mixture can be applied by conventional coating techniques such as drop-casting, draw-down, or cured in a mold. The liquid curable solution is cast directly onto the master mold and allowed to cure (e.g., cured for six (6) hours at room temperature or fifteen (15) minutes at 70° C.) to form a solid structure (i.e., first layer 32) that is then removed from the mold and then bonded to, adhered to, or encapsulated to a second layer 34 which may be made from the same or different material. For example, the first layer 32 may be made from PDMS while the second layer 34 may be made from glass. The first layer 32 may be secured to the second layer 34 using a clamp or by using one or more fasteners (e.g., bolts and nuts) that secure the two layers 32, 34 together. Alternatively, bonding through the use of an adhesive or through the use of other bonding techniques such as oxygen plasma.

In some embodiments, a sacrificial layer may be used whereby the two-part liquid curable solution is cast over the sacrificial layer wherein is then removed after curing using different stimuli or a removal agent (e.g., temperature or solvent). In this manner, the sacrificial layer is removed by melting or dissolving of the sacrificial material; leaving the microchannels 14 and constrictions 16. Glass capillaries may also be used to create the microchannels. In this method, glass capillaries (VitroCom, World Precision Instruments, Inc.) are functionalized with fluorinated silanes (e.g., PFOTS) are used as an alternative strategy to pattern a microchannel 14 with a 5 μm constriction with the two-part liquid curable solution being cast over the capillary. Using a capillary puller (Sutter Instrument Co.), glass capillaries are pulled in such a way as to fabricate a constriction in the middle of the capillary. These glass capillaries are functionalized with fluorinated silanes by vapor disposition at elevated temperatures. After functionalization, the two-part liquid curable mixture was casted around the glass capillaries and molded, as described above. After curing, the glass capillaries can be removed from the mold by pulling both ends apart to retain the constriction 16. Wires can be used in a similar process.

As an alternative to direct casting, the microfluidic substrate or chip 12 may be formed from a plurality of porous sheets or membranes are created and assembled to form the final structure. In this method, polytetrafluoroethylene (PTFE) porous membranes are used with polymethylmethacrylate (PMMA) sheet. The PTFE membranes have pore size <5 μm and thickness <1 mm. The patterns for the microchannel 14, the inlet 18, and the outlet 20 are micromachined onto the PMMA sheet and the PTFE porous membranes via laser cutting. The inlet 18 and outlet 20 are assembled with the microchannel 14 and bound together using epoxy. Fasteners such as hex screws can be used to complete device assembly. Additional details regarding the use of multiple sheets or membranes to form the device may be found in International Patent Publication No. WO 2014/145528, which is incorporated herein by reference.

Figure 4:
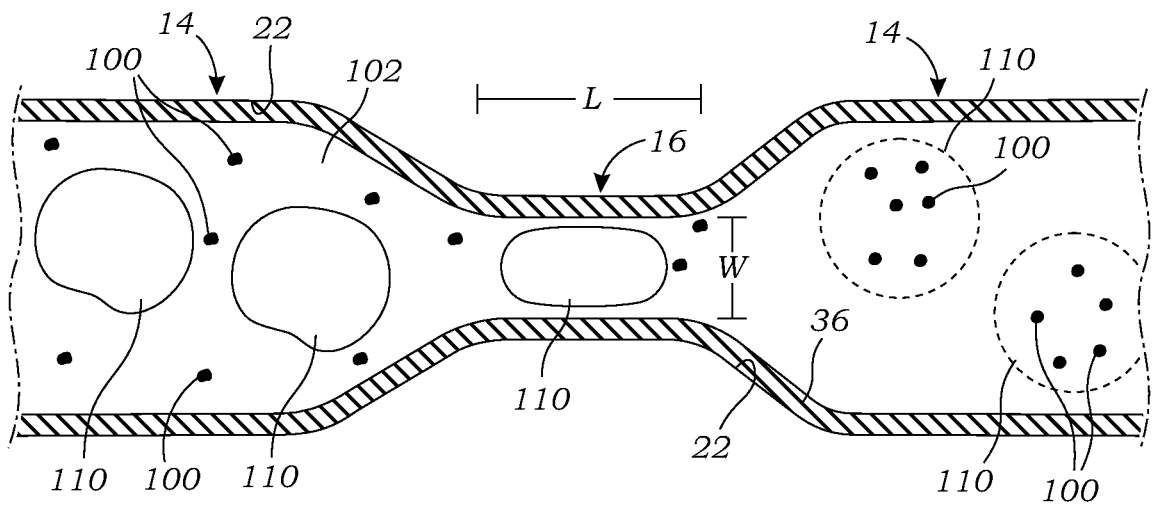
FIG. 4 illustrates one embodiment of a constriction or constriction region located in a microchannel of the microfluidic substrate or chip. In this embodiment, an omniphobic surface is created by the presence of a lubricant on the inner surface of the microchannel.

In the embodiments described above, the lubricant 36 forms a film or layer in the microchannels 14 to create the omniphobic film or layer on the surface 22 that acts as an anti-fouling and/or anti-clogging layer and prevents cells 110 from clogging in the constriction regions 16. The film of lubricant 36 also prevents fouling of the surface through, for example, the adhesion of biological molecules (e.g., proteins) to the inner surface 22 of the microfluidic device 12. FIG. 4 illustrates an embodiment, where the omniphobic layer is formed or generated on the exposed inner surfaces 22 of the microchannels 14 and constriction 16. In one embodiment, the lubricant 36 may completely fill the microchannels 14 (and constriction 16) where no or low flows of fluid are present. Upon flow of fluid 102 that contains the cells 110 and the molecules or other cargo 100, the lubricant 36 is present in a thin film or layer as illustrated to create the omniphobic contact layer on the surface 22 that prevents fouling and/or clogging of the microfluidic device 12.

Figure 5:
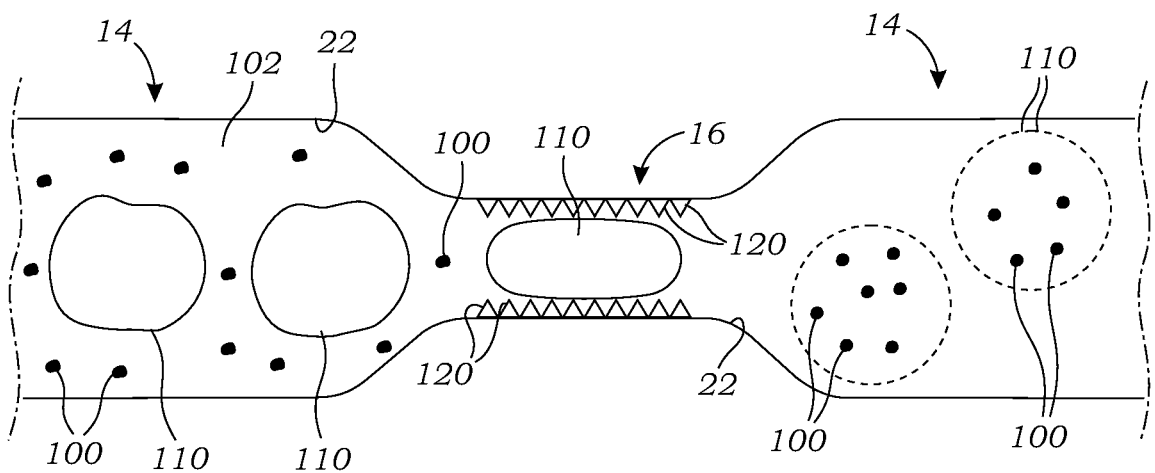
FIG. 5 illustrates another embodiment of a constriction or constriction region located in a microchannel of the microfluidic substrate or chip. In this embodiment, a plurality of nanofeatures are formed on constriction or constriction region of the microchannel.
Figure 6:
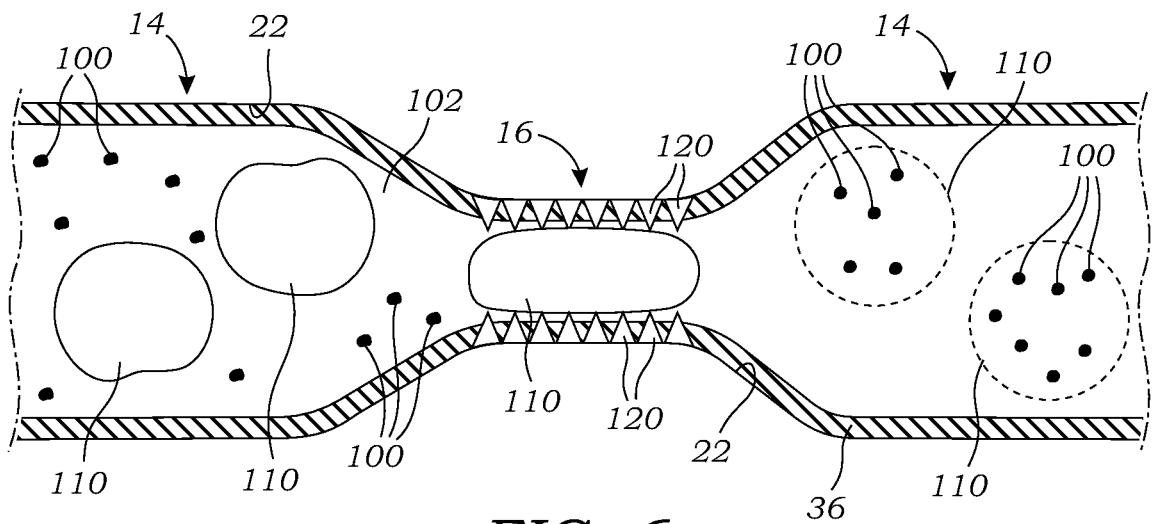
FIG. 6 illustrates another embodiment of a constriction or constriction region located in a microchannel of the microfluidic substrate or chip. In this embodiment, a lubricant is located on the inner surface of the microchannel that also contains a plurality of nanofeatures formed in the constriction or constriction region of the microchannel.

In one alternative embodiment, as illustrated in FIG. 5, the constriction 16 in the microchannel 14 contains a plurality of nanofeatures 120 that extend or otherwise project inwardly from the surface of the microchannel 14. Nanofeatures 120 are nanometer sized protrusions or protuberances that extend into the flow channel. Nanofeatures may extend into the constriction 16 for a distance of tens or hundreds of nanometers. Nanofeatures 120 may include any number of shapes of protuberances that extend into the flow path created in the constriction 16. These may include pillars, posts, wires, tubes, cones, pyramids, needles, and the like. The nanofeatures 120 may be formed using lithographic techniques including electron-beam and nanosphere lithography. In nanosphere lithography, periodic arrays of self-assembled close-packed nanospheres are used as masks to pattern underlying substrate materials. Reactive ion etching or the like may also be used to form the nanofeatures 120 with appropriate masking. The nanofeatures 120 may be formed on all exposed surfaces of the microchannel 14 and/or in the constriction region 16. Alternatively, less than all of the surfaces in the constriction 16 may contain nanofeatures 120. For example, only a single surface or two of four surfaces may contain nanofeatures 120 (e.g., top and bottom). For example, the nanofeatures 120 may be formed on silicon or glass that are then used to form the top and/or bottom of the microfluidic device 12. The nanofeatures 120 may be used without a lubricant as illustrated in FIG. 5 or, alternatively, with a lubricant as illustrated in FIG. 6. The nanofeatures 120 may be used to aid in permeabilizing the cells 110 that pass through the constrictions 16. For example, the tips or ends of the nanofeatures 120 may be sharpened to aid in physically disrupting the cell membranes of the cells 110. The nanofeatures 120 may also be functionalized to attract or repel cells 110 of certain types.

FIG. 6 illustrates an embodiment in which the nanofeatures 120 are present in the constrictions 16 along with the lubricant-formed omniphobic or superhydrophobic surface 22. In this embodiment, the lubricant on the surface 22 in conjunction with the nanofeatures 120 may impart better anti-fouling properties. Further, in one alternative embodiment, the thickness of the lubricant that is present on the surface 22 in the constriction region 16 may be adjusted to selectively expose or mask entirely the nanofeatures 120 to alter the surface characteristics or performance of the microfluidic substrate or chip 12. FIG. 6 illustrates, for example, a constriction region 16 in which the tips or ends of the nanofeatures 120 extend beyond the surface of the lubricant 36 located on the surface 22 of the constriction 16.

Figure 7:
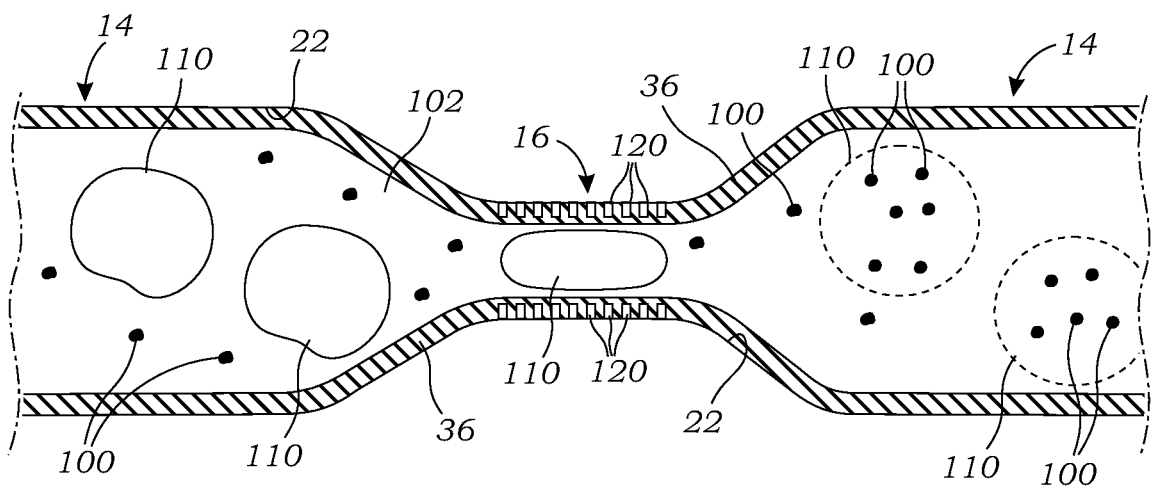
FIG. 7 illustrates another embodiment of a constriction or constriction region located in a microchannel of the microfluidic substrate or chip in which the lubricant thickness is adjustable to selectively expose or fully mask the plurality of nanofeatures that are present in the constriction in the microchannel.

FIG. 7 illustrates another embodiment in which the tips or ends of the nanofeatures 120 are fully covered by the lubricant 36 on the surface 22 so that the nanofeatures 120 are fully masked by the lubricant 36. The control of the thickness of the lubricant 36 may be adjusted in any number of ways including the choice of lubricant 36 and porosity of the material for the microfluidic device 12 as well as the flow rate through the microchannel 14. Higher flow rates may produce thinner layers of lubricant 36 while slower flow rates may be used to generate thicker layers of lubricant 36. Other approaches include incorporating a capillary or other fluidic network into the first or second layers 32, 34 that is coupled to a reservoir containing the lubricant 36 or other source and controlling the volume or pressure of lubricant 36 that is delivered to the via capillaries or fluidic network. In another approach, the level of lubricant 36 may be controlled by control of the porosity of the porous material making up the first or second layers 32, 34. This porosity may be controlled by the selection of materials used in the microfluidic substrate or chip 12 or by adjusting the effective pore sizes by adjusting the compressive force (e.g., by adjusting fasteners, clamps, external pressure, or the like) that pinch or sandwich the layers 32, 34 (e.g., PTFE layer). In yet another alternative for controlling the thickness of the lubricant 36, a capillary-stabilized liquid may be used as a reversible, reconfigurable gate to modulate the level of lubricant 36 in on the surface 22 of the constriction. Details regarding the liquid-based gating mechanism may be found in Hou et al., Liquid-based gating mechanism with tunable multiphase selectivity and antifouling behavior, Nature, Vol. 159 (March 2015), which is incorporated herein by reference.

Figure 8:
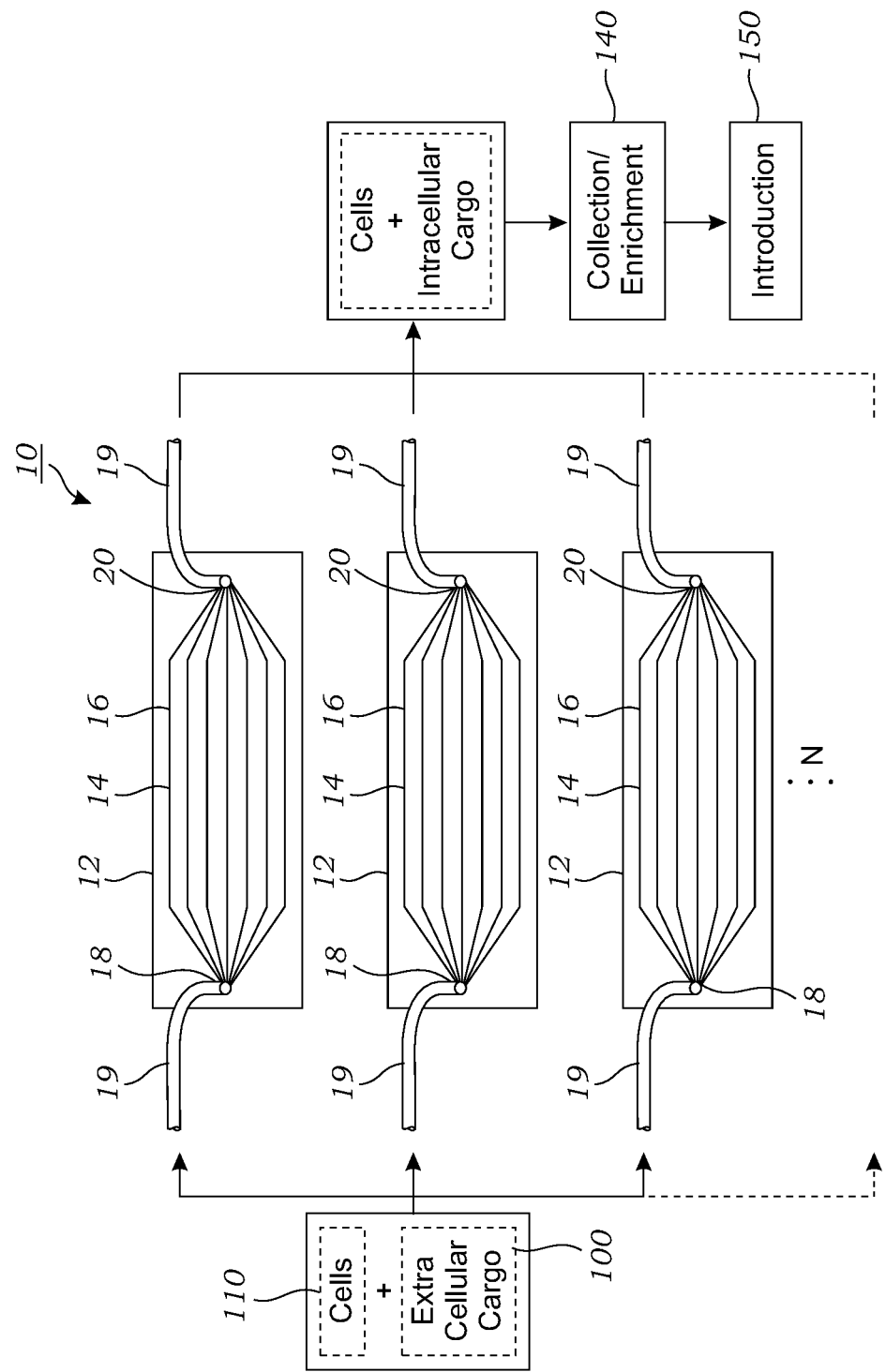
FIG. 8 schematically illustrates a microfluidic-based system for the intracellular transport of molecules or other cargo into cells that uses a plurality of microfluidic substrates or chips in parallel to process large numbers of cells.

FIG. 8 illustrates a schematic representation of a microfluidic-based system 10 for the intracellular transport of molecules or other cargo 100 into cells 110. As seen in FIG. 8, the cells 110 and the molecules or other cargo 100 are run through one or more microfluidic substrates or chips 12. In this particular embodiment, a plurality of microfluidic substrates or chips 12 (N is the total number of microfluidic substrates or chips 12) are employed in parallel so that large numbers of cells 110 may be processed. As explained herein, according to one preferred embodiment of the invention, flow rates that achieve processing rates of cells 110 between about 50 and about 100,000 cells/sec/microchannel may be achieved. Preferably, the microchannel 14 and the constriction region 16 remain unclogged after the passage and sustainable processing (i.e., the cells 110 remain live) of $1\times10^6$ cells, and more preferably more than $1\times10^7$, $1\times10^8$, and $1\times10^9$ cells through the microchannel 14.

The cells 110 may be obtained from a mammalian subject, for example, a human. The cells 110 may include, as one example, stem cells or cells with stem like properties that are obtained for example, from the bone marrow of a subject. In one preferred embodiment, the cells 110 are living cells and remain living after intracellular delivery of the molecules or other cargo 100. The cells 110 may also include immune cells that are obtained from a subject. An example includes T-lymphocytes that are obtained from the subject for adoptive cellular therapies. The invention is not, however, limited to use with stem cells or immune cells. In other embodiments, healthy cells 110 may also be run through the system 10. As noted herein, the cells 110 are run through the microfluidic substrates or chips 12 along with the molecules or other cargo 100 that are to be intracellularly transported into the cells.

The permeablized cells that uptake the molecules or other cargo 100 are then captured or collected after passing through the microfluidic substrates or chips 12. This is illustrated in operation 140 in FIG. 8. For example, the outlets 20 may be coupled to a collection container (not shown) or other receptacle (e.g., bag, vial(s), bottle(s) which may be used to enrich the concentration of collected cells 110 that are processed using the system 10. In one embodiment, for example, where the molecules or other cargo 100 include gene-modification components, the collected cells 110 that have been modified genetically may then be introduced into a subject as seen in operation 150. The subject that receives the processed cells 110 may be the same individual that provided the cells 110 that were initially processed with the system 10. Alternatively, the recipient of the cells 110 may be a different subject from the source of cells 110 that are run through the system 10.

While embodiments of the present invention have been shown and described, various modifications may be made without departing from the scope of the present invention. The invention, therefore, should not be limited except to the following claims and their equivalents.

What is claimed is:
1. A microfluidic device for processing cells comprising:
a plurality of porous substrates or chips, each porous substrate or chip comprising an inlet, an outlet, and a plurality of microchannels disposed in the porous substrate or chip and fluidically coupled to the inlet and the outlet, wherein the inlets of the plurality of porous substrates or chips are configured to receive a solution containing the cells as well as molecules or other cargo to be delivered intracellularly to the cells, each of the plurality of microchannels containing a constriction region therein, wherein the plurality of microchannels including the constriction region each comprise one or more omniphobic, superhydrophilic, or superhydro- phobic surfaces having a plurality of sharpened protuberances extending from the one or more surfaces;

a lubricant that is immiscible with the solution containing the cells disposed in the plurality of porous substrates or chips and forming a lubricant film over the one or more omniphobic, superhydrophilic, or superhydrophobic surfaces; and wherein respective ends of the sharpened protuberances extend beyond the lubricant and into the respective microchannels in the constriction regions of the plurality of microchannels.

2. The microfluidic device of claim 1, wherein each of the plurality of microchannels comprises multiple constriction regions therein.

3. The microfluidic device of claim 1, further comprising a pump coupled to the inlets of the plurality of porous substrates or chips, the pump configured to pump the cells and solution into the inlets of the plurality of porous substrates or chips.

4. The microfluidic device of claim 3, wherein the solution containing the cells also contains the molecules or other cargo to be intracellularly delivered into the cells.

5. The microfluidic device of claim 3, each porous substrate or chip further comprising a second inlet fluidically coupled to the plurality of microchannels, wherein the second inlets are coupled to a second pump configured to pump a solution containing the molecules or other cargo to be intracellularly delivered into the cells.

6. The microfluidic device of claim 1, wherein each constriction region has a width of less than 10 µm.

7. The microfluidic device of claim 1, wherein the sharpened protuberances comprise nanometer-sized protuberances shaped as one or more of wires, cones, pyramids, and needles.

8. The microfluidic device of claim 1, wherein the sharpened protuberances are disposed on the one or more surfaces within each constriction region.

9. The microfluidic device of claim 1, wherein each porous substrate or chip further comprises a first layer and a second layer and a fastener or clamp contacting the first layer and second layer and configured to compress each porous substrate or chip to adjust a thickness of the lubricant film.

10. A system for processing cells using a plurality of microfluidic devices of claim 1, comprising one or more pumps configured to simultaneously pump the solution containing the cells and molecules or other cargo to be intracellularly transported into the cells through the plurality of microfluidic devices.

* * * * *